United States Patent [19]

Sprague et al.

[11] Patent Number: 4,542,160
[45] Date of Patent: Sep. 17, 1985

[54] METHOD OF USE OF BICYCLOHEPTANE SUBSTITUTED PROSTAGLANDIN ANALOGS AS CARDIOVASCULAR AGENTS

[75] Inventors: Peter W. Sprague; Melanie J. Loots, both of Pennington; Martin F. Haslanger, Lambertville, all of N.J.

[73] Assignee: E. R. Squibb & Sons, Inc., Princeton, N.J.

[21] Appl. No.: 635,980

[22] Filed: Jul. 30, 1984

[51] Int. Cl.[4] .................. A61K 31/19; A61K 31/21
[52] U.S. Cl. .................... 514/569; 514/510; 514/559; 514/573; 514/826
[58] Field of Search ............... 424/317, 305; 562/502; 514/510, 569

[56] References Cited

U.S. PATENT DOCUMENTS

| | | | |
|---|---|---|---|
| 3,946,065 | 3/1976 | Matsui et al. | 562/502 X |
| 4,073,933 | 2/1978 | Shimomura et al. | 426/299 |
| 4,143,054 | 3/1979 | Sprague | 562/502 X |
| 4,436,934 | 3/1984 | Larock | 562/502 |
| 4,458,091 | 7/1984 | Jones et al. | 562/502 |

*Primary Examiner*—Leonard Schenkman
*Attorney, Agent, or Firm*—Lawrence S. Levinson; Burton Rodney

[57] ABSTRACT

Bicycloheptane substituted prostaglandin analogs are provided having the structural formula

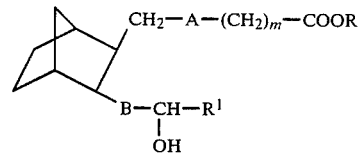

and including all stereoisomers thereof.

The compounds are cardiovascular agents useful, for example, in the treatment of thrombolytic disease.

11 Claims, No Drawings

METHOD OF USE OF BICYCLOHEPTANE SUBSTITUTED PROSTAGLANDIN ANALOGS AS CARDIOVASCULAR AGENTS

DESCRIPTION OF THE INVENTION

The present invention relates to bicycloheptane substituted prostaglandin analogs which are cardiovascular agents useful, for example, in the treatment of thrombolytic disease. These compounds have the structural formula

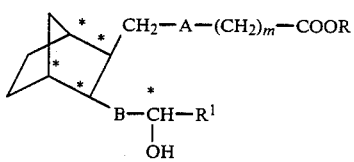

I and including all stereoisomers thereof, wherein A is $CH_2$—$CH_2$ or CH=CH—; m is 0 to 5; R is H, lower alkyl, alkali metal or tris(hydroxymethyl)aminomethane; B is —CH=CH— or —$(CH_2)_2$—; and $R^1$ is alkyl, aryl, aralkyl, cycloalkyl or cycloalkylalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term $(CH_2)_m$ includes straight or branched chain radicals having from 1 to 7 carbons in the normal chain and may contain one or more lower alkyl substituents. Examples of $(CH_2)_m$ groups include

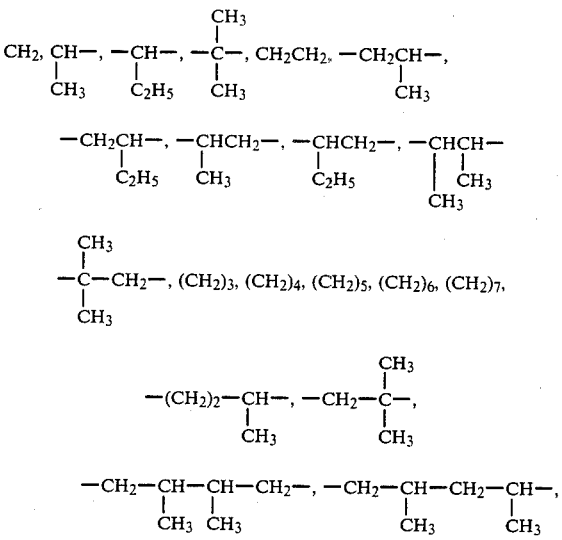

The term "halogen" or "halo" as used herein refers to chlorine, bromine, fluorine or iodine with chlorine being preferred.

Preferred are those compounds of formula I wherein A is a —CH=CH—, m is 2 or 4, B is CH=CH, R is H, and $R^1$ is aralkyl such as benzyl or 1-methylbenzyl or cycloalkyl, such as cyclohexyl.

The compounds of formula I of the invention may be prepared as described below and as shown in the following reaction sequence.

A. Where A is CH=CH

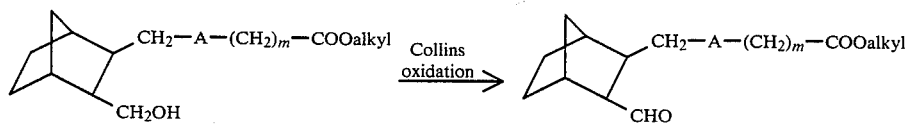

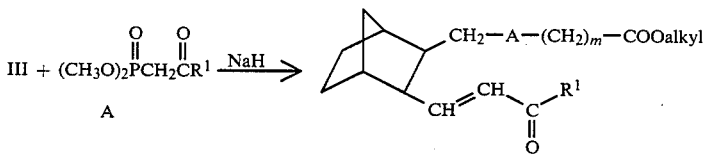

IV (where A is —CH=CH—)

-continued
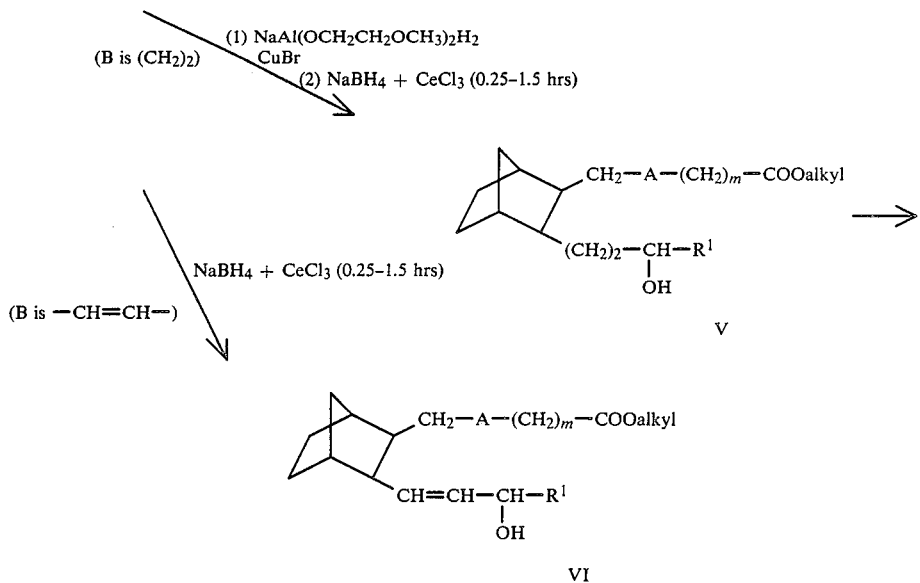
B. Where A is CH$_2$—CH$_2$
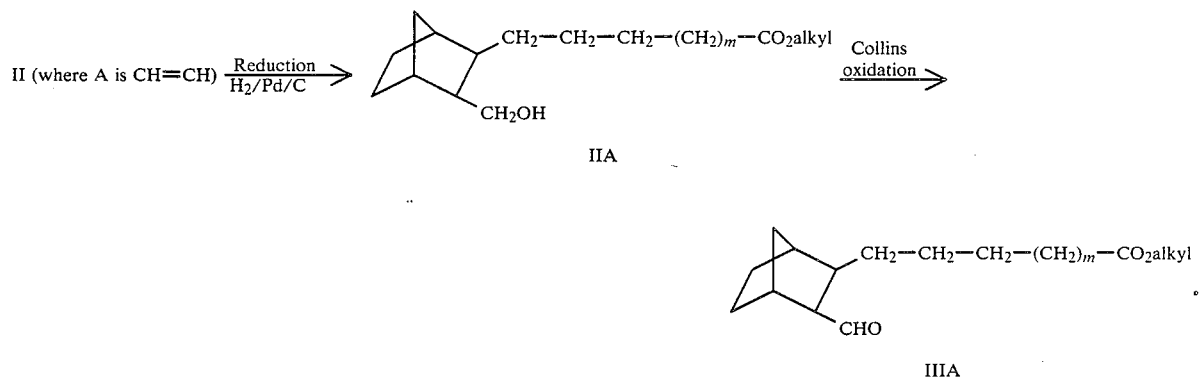
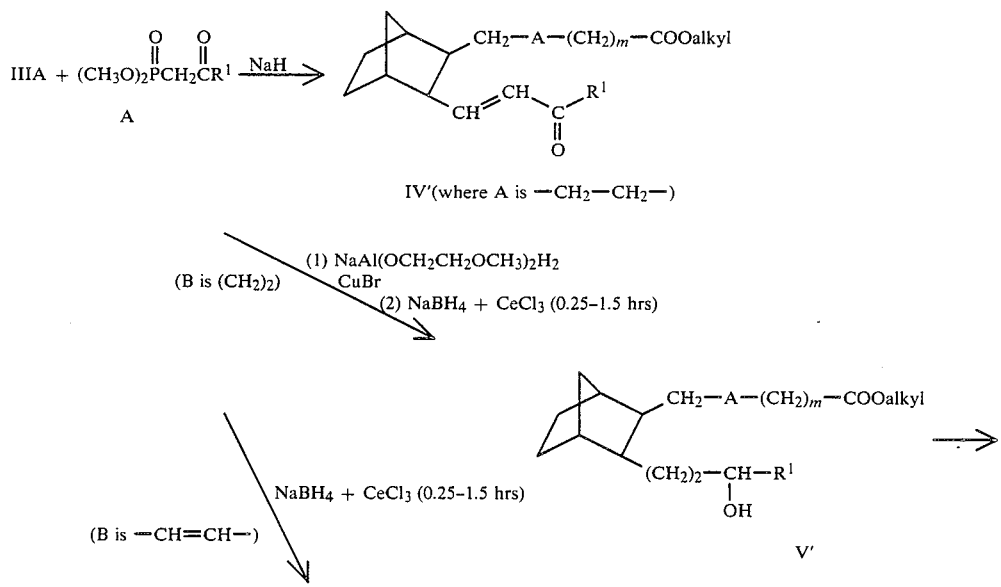

-continued

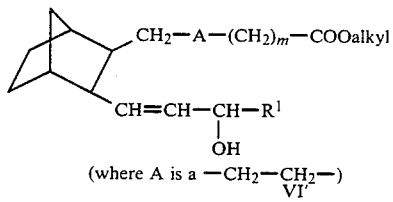

(where A is a —CH$_2$—CH$_2$—)
VI'

V, VI V', VI' $\xrightarrow[\text{Alkali metal hydroxide}]{\text{Hydrolysis}}$
(LiOH, NaOH, KOH)

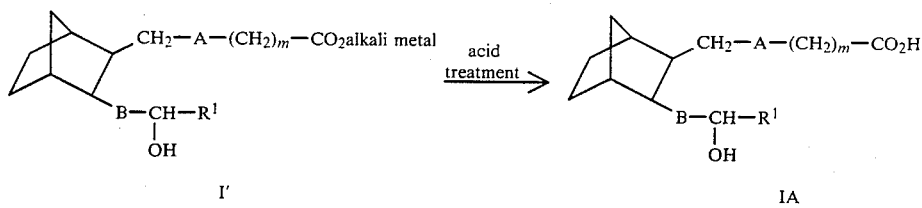

Referring to reaction sequence "A", the starting lower alkyl ester containing the hydroxymethyl group (that is, compoound II) is subjected to a Collins oxidation, for example, by reacting II with chromium oxide in pyridine to form aldehyde III of the structure

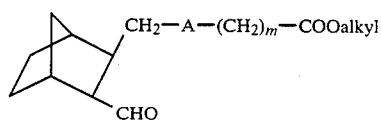     III

Aldehyde III is reacted with a dialkoxy phosphonate, such as of the structure

     A employing a molar ratio of III:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

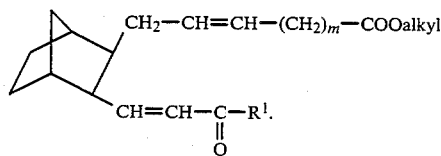     IV

Compound IV may then be reduced by two different ways as outlined above to form compounds V or VI

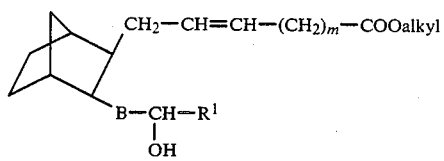

V - B is (CH$_2$)$_2$

-continued
VI - B is —CH=CH—

Thus, to form compound V wherein B is (CH$_2$)$_2$, compound IV is first reacted with NaAl(OCH$_2$CH$_2$OCH$_3$)$_2$H$_2$ in the presence of CuBr and then the reaction product is reduced, for example, by treating with a reducing agent such as sodium borohydride or sodium cyanoborohydride in a solvent such as methanol and in the presence of cerium trichloride for a period of from about 0.25 to about 1.5 hours to form compounds of formula V.

Compounds of the invention wherein A is —CH$_2$—CH$_2$— or a single bond may be prepared as shown in reaction sequences B and C by reducing starting hydroxymethyl compound II by treating with hydrogen in the presence of a palladium on carbon catalyst to form compound IIA and subjecting IIA (or II' where A is a single bond) to a Collins oxidation reaction to form the corresponding aldehyde IIIA or III' which is then reacted with dialkoxy phosphonate A as described above to form corresponding enone compound IV' which is then reduced as described hereinbefore to form the ester compounds V' or VI'.

Esters V, VI, V' and VI' may be hydrolyzed to the corresponding acid by treating the esters with an alkali metal hydroxide, such as lithium or sodium hydroxide in the presence of an inert solvent such as tetrahydrofuran, methanol or dimethoxyethane-water to form the alkali metal salt followed by neutralizing with an acid, such as dilute hydrochloric acid or oxalic acid to form the acid IA.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The starting lower alkyl ester II and II' may be prepared according to the following reaction sequences.

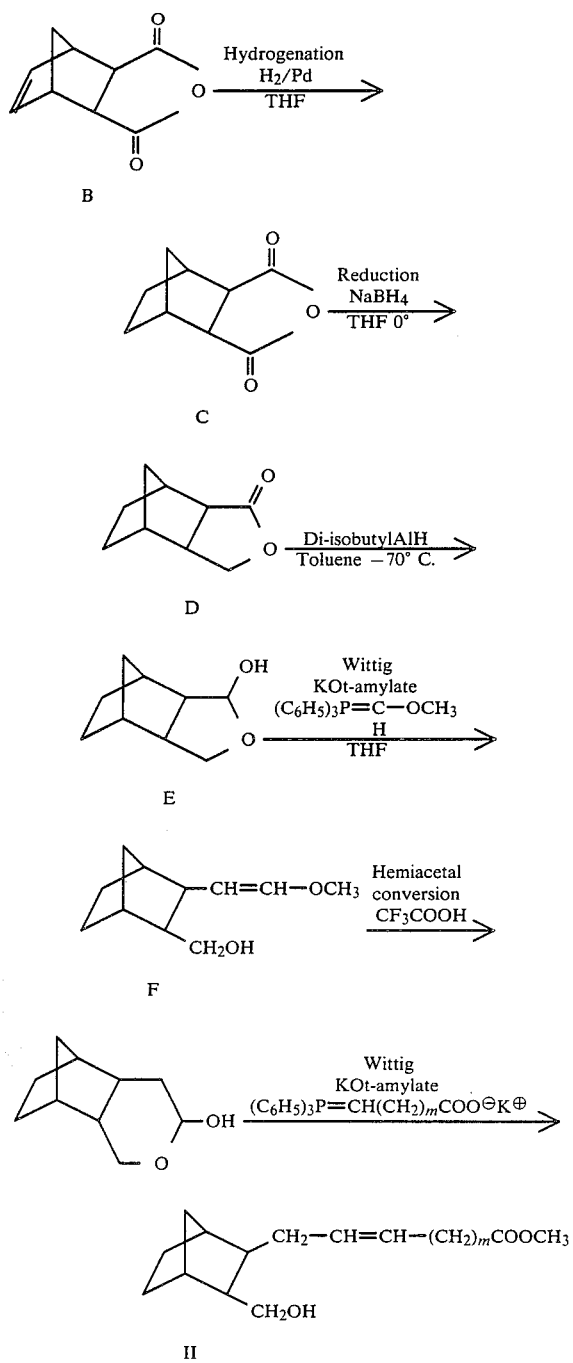

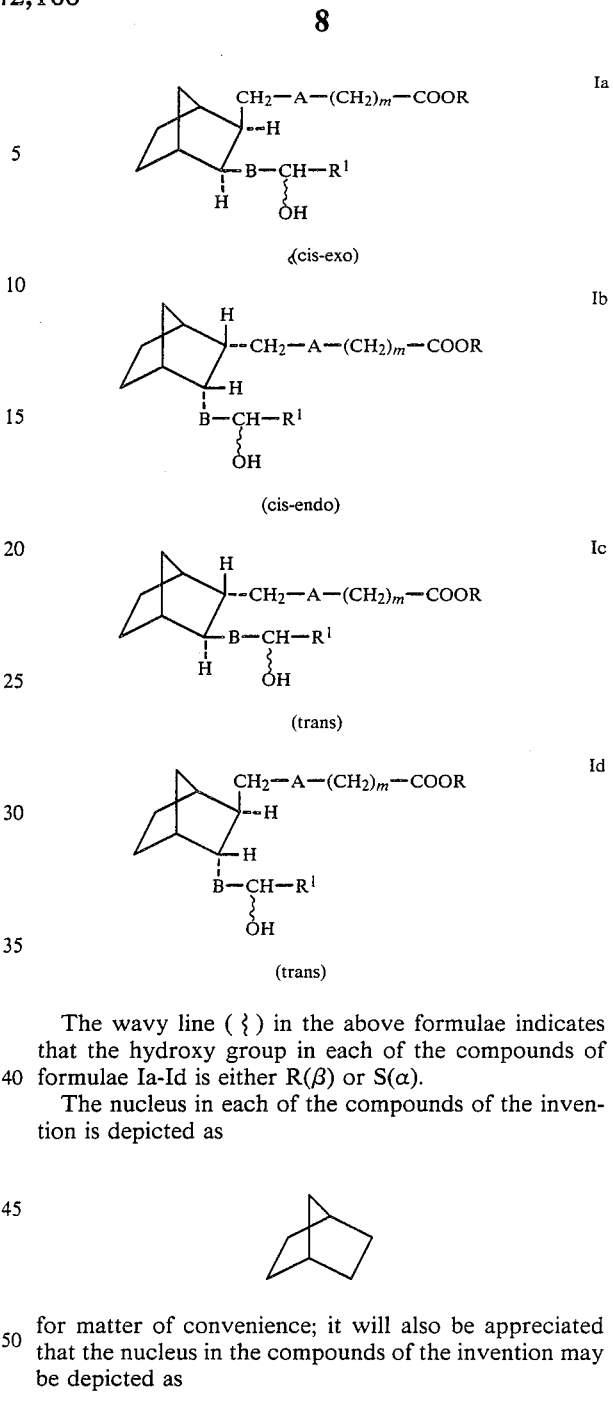

The wavy line ( ⌇ ) in the above formulae indicates that the hydroxy group in each of the compounds of formulae Ia-Id is either R($\beta$) or S($\alpha$).

The nucleus in each of the compounds of the invention is depicted as for matter of convenience; it will also be appreciated that the nucleus in the compounds of the invention may be depicted as The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisometric pairs may be prepared as shown in the working Examples which follow and by employing starting materials and following the procedures as outlined in U.S. Pat. No. 4,143,054. Examples of such stereoisomers are set out below.

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain numbers additionally serve as intermediates for other members of the group.

The following Examples represent preferred embodiments of the invention. Unless otherwise indicated, all temperatures are expressed in degrees Centigrade.

EXAMPLES 1 AND 2

[1α,2β(Z),3β(1E,4S),4α]-7-[3-(3-Hydroxy-4-phenyl-1-pentenyl)bicyclo[2.2.1]hept-2-yl]-5-heptenoic acid (fast moving isomer A) and

[1α,2β(Z),3β(1E,4S),4α]-7-[3-(3-Hydroxy-4-phenyl-1-pentenyl)bicyclo[2.2.1]hept-2-yl]-5-heptenoic acid (fast moving isomer B)

A.

exo-5-Norbornene-2,3-dicarboxylic anhydride 400 g (2.44 mole) of endo-5-norbornene-2,3-dicarboxylic anhydride was melted and heated in an open beaker to 190° for one hour and then cooled by pouring into a thin layer on the bottom of several crystallizing dishes. The resulting solid was scraped up before it cooled completely and recrystallized 5 times from benzene to give 75 g (0.046 mole) of pure exo-5-norbornene-2,3-dicarboxylic anhydride (19%), m.p. 143°.

B.

(exo)-Hexahydro-4,7-methanoisobenzofuran-1,3-dione

To a solution of 1.5 g (9.1 mmol) Part A cis exo isomer in 125 ml THF, was added 100 mg 10% Pd/C. The mixture was stirred under atmospheric hydrogen pressure until hydrogen uptake ceased, then filtered and concentrated to give an oily white solid. This was dissolved in Et$_2$O and reconcentrated to give 1.54 g of white solid (quantitative).

C.

(3aβ,4α,7α,7aβ)-exo-Octahydro-4,7-methanoisobenzofuran-1(3H)one

To a suspension of 0.37 g (0.0098 mole) of NaBH$_4$ in 25 ml dry THF under N$_2$ was added 1.54 g (0.0093 mole) of Part B compound, all at once, with some foaming. The reaction mixture was stirred at 0°–3° C. for 4 hours. The THF was removed in vacuo and the white solid obtained was added slowly to a beaker of ice, with stirring and fizzing. The cloudy white solution obtained was acidified to pH 2 and extracted 6×15 ml CH$_2$Cl$_2$. The combined CH$_2$Cl$_2$ extracts were dried over MgSO$_4$, filtered and concentrated to give 1.13 g of title lactone as a clear oil (0.0083 mole, 89%).

D.

(3aβ,4α,7α,7aβ)-exo-Octahydro-4,7-methanoisobenzofuran-1-ol

In a one-liter flask under N$_2$, 10.48 g (68.9 mmol) of the Part C lactone was dissolved in 150 ml B&J toluene and cooled to −70°. Over 1 hour, 144 ml of 1N diisobutyl aluminum hydride (DIBAH) in hexane was added (144 mmol) dropwise, keeping the reaction temperature at −65°. The mixture was stirred 30 minutes at −70°. A solution of 9 ml of acetic acid in 56 ml toluene was added over 10 minutes as the reaction temperature rose to −50°. It was allowed to warm to −30°, and 73 ml of 10% HCl was added, keeping the temperature below 0°. Then the reaction mixture was allowed to warm to room temperature.

The toluene/hexane and water layers were separated. The water layer was extracted 5×50 ml CHCl$_3$. Then the combined organic layers were washed with standard NaHCO$_3$ and dried over MgSO$_4$. The solution was filtered and concentrated in vacuo to give 9 g of title hemiacetal, a pale yellow oil (58.4 mmol) 85%.

E.

(exo)-(1α,2β,3β,4α)-2-(3-Hydroxymethyl)bicyclo[2.2.1]hept-2-yl methoxyethylene

At 0° under N$_2$, 41.96 g (0.122 mole) of methoxymethyl triphenyl phosphonium bromide (Aldrich) was suspended in 115 ml dry THF. Keeping the temperature below 5°, 71.3 ml of 1.44M potassium t-amylate solution in toluene was added dropwise. The mixture was stirred 1 hour at 0°, giving a homogeneous, deep red solution. A solution of 7.6 g (0.0493 mole) of Part D compound in 10 ml THF was added over 5 minutes. The reaction mixture was stirred 2 hours at room temperature. After cooling to 5°, 4.8 ml (3.78 g, 0.086 mole) of acetaldehyde was added. The temperature of the reaction rose to 13°. Water (100 ml) was added and the reaction mixture was neutralized to pH 7 with 10% HCl.

The organic and aqueous layers were separated. The aqueous layer was extracted 5 times with 75 ml Et$_2$O. The combined organics were dried over MgSO$_4$, filtered, and concentrated to a yellow oil. This was stirred with 150 ml diisopropyl ether. Precipitated triphenyl phosphine oxide was filtered off and the precipitate was washed well with ether. The filtrate was concentrated to a yellow oil (20 g). This was purified on a flash column, using 20% ethyl acetate in hexane as eluant to give 5.8 g of title enol ether (0.318 mole, 64.5%).

F.

(4β,5α,8α,8aβ)-exo-Octahydro-5,8-methano-1H-benzopyran-3-ol

The Part E enol ether (0.81 g, 0.0044 mole) was stirred in 15 ml 20% aqueous trifluoroacetic acid for 1 hour under N$_2$. The mixture was diluted with 40 ml ether and neutralized by addition of solid NaHCO$_3$. The product was extracted with three 30 ml portions of ether. The combined ether extracts were dried over MgSO$_4$, filtered, and concentrated to give 0.68 g (0.004 mole) of title hemi-acetal (91%).

G.

(1α,2β(Z),3β,4α)-7-[(3-Hydroxymethyl)bicyclo[2.2.1]hept-2-yl]-5-heptenoic acid, methyl ester At 0°, under N$_2$, 2.45 g (0.0146 mole) of Part F hemiacetal and 9.5 g (0.0215 mole) of carboxybutyl triphenylphosphonium bromide were suspended in 60 ml toluene. Over 90 minutes, 29.3 ml of 1.42M potassium t-amylate, in toluene (0.0417 mole) was added. The mixture was stirred for 30 minutes at 0°, then at room temperature overnight.

A solution of 2.35 ml (2.57 g, 0.043 mole) of acetic acid in 30 ml toluene was added dropwise while cooling the reaction mixture in an ice bath. Then 42 ml of water was added. A thick suspension formed. The mixture was acidified to pH 2.5 with concentrated HCl. It was then diluted with 42 ml ethyl acetate, 10 g of NaCl was added, and it was seeded with starting phosphonium salt and stirred for several hours. Precipitated phosphonium salt was then filtered off and washed well with ethyl acetate.

The toluene/ethyl acetate layer was separated from the water layer, and the water layer extracted with ethyl acetate. The combined organics were dried over MgSO$_4$, filtered, and concentrated to a thick oil. This was seeded with (C$_6$H$_5$)$_3$P=O and stirred several hours with 50 ml 5% K$_2$CO$_3$. It was filtered and reseeded several times to remove as much phosphorus impurity as possible. Then the aqueous filtrate was extracted 12 times with 50/50 toluene/ether. The aqueous layer was chilled and acidified slowly with concentrated HCl to pH 2.5. It was then extracted with ethyl acetate (2×50 ml, 2×25 ml). The combined ethyl acetate extracts were dried over MgSO$_4$, filtered, and concentrated to give 2.4 g of a yellow oil, which contained the desired product and phosphorus impurities.

This oil was dissolved in 20 ml ether/CH$_3$OH and treated with diazomethane in ether until no evolution of N$_2$ was observed. Excess diazomethane was destroyed by addition of acetic acid. The ether solution was washed with 2×5 ml saturated NaHCO$_3$, and dried over MgSO$_4$, filtered and concentrated in vacuo. The product was purified on a flash column, using 20% EA/hexane as eluant, giving 1.2 g (0.0045 mole) of title hydroxymethyl compound, 31% yield from the Part E enol ether.

H.
(1α,2β(Z),3β,4α)-7-[(3-Formyl)bicyclo[2.2.1]hept-2-yl]-5-heptenoic acid, methyl ester Under N$_2$, at room temperature, 6 g (0.006 mole) of CrO$_3$ was gradually added to a mixture of 0.97 ml (0.949 g, 0.012 mole) pyridine and 30 ml dichloromethane. The mixture was stirred for 30 minutes, giving a rust red solution. Celite (1.97 g) was added, followed by 0.27 g (1 mmol) of title G hydroxymethyl compound. The mixture was stirred for 30 minutes at room temperature, then filtered through Celite on a frit, washing the Celite well with dichloromethane. The filtrate was washed with 2×20 ml saturated NaHCO$_3$, 2×20 ml 10% HCl, then 1×20 ml saturated NaHCO$_3$. It was dried over MgSO$_4$, filtered and concentrated in vacuo. It was necessary to redissolve in Et$_2$O and filter through silica gel on a frit to remove Cr salts. A partially solid oil (150 mg) which nmr showed to be the (0.6 mmol) desired title aldehyde, was obtained (57%).

I.
[1α,2β(Z)3β(1E,4S),4α]-7-[3-(3-Oxo-4-phenyl-1-pentenyl)bicyclo[2.2.1]hept-2-yl]-5-heptenoic acid, methyl ester (1) (+) Methyl 2-phenylpropionate (+) 2-Phenylpropionic acid (8.4 g, 56 mmol) in methanol (180 ml) and concentrated H$_2$SO$_4$ (2 ml) were heated at reflux for 4 hours. The reaction was cooled down to room temperature and concentrated in vacuo (∼100 ml). The products were extracted with Et$_2$O (150 ml×3), which was washed with saturated NaHCO$_3$, H$_2$O and dried over MgSO$_4$. Filtration and evaporation of solvent yielded a yellow oil (8.9 g), which was distilled to give (+) methyl 2-phenylpropionate as a colorless oil (8.34 g, 51 mmol, 91%, b.p. 73° C./1.5 mm Hg), [α]$^D$ = +111° (c=2, toluene).

(2) (+) 2-Oxo-3-phenylbutyl dimethyl phosphonate n-Butyllithium (1.6M, 62.5 ml, 100 mmol) was added dropwise to a magnetically stirred solution of dimethyl-methyl phosphonate (12.4 g, 100 mmol) in THF (90 ml) at −78° C. Stirring was continued for 30 minutes at −78° C. Then Part I (1) ester (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5–6. The solvent was removed in vacuo and H$_2$O (100 ml) was added. The products were extracted with CH$_2$Cl$_2$ (100 ml×3), which was washed with saturated NaHCO$_3$, H$_2$O and dried over MgSO$_4$. Filtration and evaporation of solvent left a yellow oil. This was fractionated to give (+)2-oxo-3-phenylbutyl dimethyl phosphonate (8.1 g, 31.6 mmol, 63%, b.p. 142°–144°/0.2 mm Hg), [α]$^D$ = +235° (c=2, toluene).

(3)
[1α,2β(Z),3β(1E,4S),4α]-7-[3-(3-Oxo-4-phenyl-1-pentenyl)bicyclo[2.2.1]hept-2-yl]-5-heptenoic acid, methyl ester Under N$_2$, 0.154 g (0.0038 mole) of 59.2% NaH in mineral oil was suspended in 12 ml dry THF and cooled to 5°. A solution of 1.06 g (0.0042 mole) of the chiral (+)2-oxo-3-phenylbutyl dimethyl phosphonate was added dropwise and stirred until a homogeneous pale yellow solution was obtained. A solution of the title H aldehyde in 3 ml THF was then added dropwise over 2 minutes. The mixture was stirred at room temperature for 2.5 hours. TLC showed a mixture of product and starting material, and so stirring was continued overnight.

The reaction was quenched with 0.46 ml acetic acid and poured into 40 ml ether, washed with 5% NaHCO$_3$, water and brine. The water layers were back-extracted with ether. The combined ether layers were dried over MgSO$_4$, filtered, and concentrated in vacuo. Flash chromatography of the resulting oil (1.4 g) using 50% EA/hex gave 740 mg of title enone compound (0.0019 mole, 50% yield from title G hydroxymethyl compound).

Close examination showed this to be a mixture of cis and trans enone. It was purified on a flash column, using 5% ethyl acetate in hexane as eluant, to give 600 mg of the pure title trans enone, 40% from title G hydroxymethyl compound.

J.
[1α,2β(Z),3β(1E,4S),4α]-7-[3-(3-Hydroxy-4-phenyl-1-pentenyl)bicyclo[2.2.1]hept-2-yl]-5-heptenoic acid, methyl ester Sodium borohydride (58 mg, 0.0015 mole) was added to a solution of 600 mg (0.0015 mole) title I enone and 580 mg CeCl$_3$·7H$_2$O (0.0015 mole) in 15 ml methanol and 1.3 ml THF at 0°. The mixture was stirred for 8 minutes at 0° and then poured into 130 ml of saturated ammonium chloride solution. The product was extracted with ethyl acetate. The ethyl acetate extract was dried over $MgSO_4$, filtered and concentrated to give 527 mg of a mixture of 4 diastereomers (1.37 mmol, 92% from title I enol).

These were not completely separable on either tlc or the semiprep column on the hplc, packed with 50μ silica gel. Four mixtures of title J diastereomers were obtained.

K.

[1α,2β(Z),3β(1E,4S),4α]-7-[3-(3-Hydroxy-4-phenyl-1-pentenyl)bicyclo[2.2.1]hept-2-yl]-5-heptenoic acid (fast moving isomer A) and

[1α,2β(Z),3β(1E,4S),4α]-7-[3-(3-Hydroxy-4-phenyl-1-pentenyl)bicyclo[2.2.1]hept-2-yl]-5-heptenoic acid (fast moving isomer B)

title J ester was stirred in 5:2:1 $THF:1N\ LiOH:H_2O$. Methanol was added dropwise to keep the mixture homogeneous. When tlc showed disappearance of starting ester, the mixture was poured into saturated NaCl and acidified to pH 2.5. The acid was extracted with ethyl acetate and dried over $MgSO_4$, filtered, and concentrated in vacuo.

The 4 mixtures of title J diastereomers were all hydrolyzed separately and the resulting mixtures were chromatographed on a semiprep column on the analytical hplc, using a gradient from 0.25→0.5% $CH_3OH$ in $CH_2Cl_2$. TLC of fractions obtained then allowed combination of like fractions. It was necessary to develop tlc plates 3-4 times with 4% $CH_3OH$ in $CH_2Cl_2$ to see separations. Pure samples were obtained of the two fast moving isomers, $fmi_a$ and $fmi_b$ (Examples 1 and 2, respectively). The two slower moving isomers were not obtained in pure form. Chromatography yielded 42.5 mg, 0.11 mmol, 8% from the title J ester.

EXAMPLES 3 AND 4

[1α,2α(Z),3β(1E),4α]-7-[3-(3-Cyclohexyl-3-hydroxy-1-propenyl)bicyclo[2.2.1]hept-2-yl]-5-heptenoic acid (fast moving isomer) and

[1α,2α(Z),3β(1E),4α]-7-[3-(3-Cyclohexyl-3-hydroxy-1-propenyl)bicyclo[2.2.1]hept-2-yl-5-heptenoic acid (slow moving isomer)

A.
(endo)-Hexahydro-4,7-methano-isobenzofuran-1,3-dione

Endo-5-norbornene-2,3-dicarboxylic anhydride (Kodak) (8.1 g, 0.05 mole) was dissolved in 300 ml THF and stirred under atmospheric $H_2$ pressure until uptake of $H_2$ ceased. The THF solution was filtered through a pad of celite on a glass frit and concentrated to give 8.1 g title anhydride in the form of a white solid (100%).

B.
(3aα,4α,7α,7aα)-endo-Octahydro-4,7-methano-isobenzofuran-1(3H)one

The title A anhydride (8.1 g, 0.0487 mole) was added slowly in a stream of $N_2$ to a suspension of 1.9 g $NaBH_4$ (0.0502 mole) in 120 ml THF at 0°. The mixture was stirred 4 hours at 0°, then slowly poured into ice with stirring. Some THF was removed on the rotary evaporator. The reaction mixture was then extracted with $CH_2Cl_2$. The combined extracts were dried over $MgSO_4$, then filtered and concentrated to give 6.6 g of title B endo-lactone (0.0434 mole, 89%).

C.
(3aα,4α,7α,7aα)endo-Octahydro-4,7-methanol-isobenzofuran-1-ol

The title B endo-lactone (6.6 g, 0.0434 mole) was dissolved in 100 ml toluene under $N_2$ and cooled to −70°. Keeping the temperature <−65°, 90.5 ml of 1M DIBAH in hexane was added over 30 minutes. The mixture was stirred 30 minutes at −70°. Then a solution of 5.6 ml acetic acid (0.098 mole) in 35 ml toluene was added (with foaming) at this temperature.

The reaction mixture was warmed to −30° and 46 ml of 10% HCl was added, keeping the temperature below 0°. The reaction was then warmed to room temperature.

The toluene/hexane layer was separated, washed with 5% $NaHCO_3$ and dried over $MgSO_4$. It was filtered and concentrated to give 3.7 g title C compound. The water layer was extracted with toluene, which yielded an additional 0.3 g title C compound. Total 4 g, 0.259 mole, 60%.

D.
(endo)-(1α,2α,3α,4α)-2-(3-Hydroxymethyl)bicyclo[2.2.1]hept-2-yl-methoxyethylene Under nitrogen atmosphere, 28.95 g of methoxymethyl triphenyl phosphonium chloride (0.0844 mole) was suspended in 90 ml dry THF and cooled to 0°. Potassium t-amylate (49.2 ml of 1.44M solution in toluene)(0.0708 mole) was added dropwise over 20 minutes. The mixture was stirred 90 minutes at 0°. A solution of 5.25 g title C compound in 20 ml THF was added. The mixture was allowed to warm to room temperature and stirred 3 hours at room temperature.

3.1 ml of acetaldehyde was added, and the reaction mixture neutralized to pH 7 using 10% HCl, after adding 20 ml $H_2O$. The solution was extracted with ether. Combined ether extracts were dried over $MgSO_4$, filtered, and concentrated to an oil which was stirred overnight with diisopropyl ether to precipitate phosphorus-containing impurities. These were filtered off, and the solution concentrated to give an oil, which was purified by flash chromatography, using 20% ethyl acetate in hexane as eluant, to give 3.45 g (0.02 mole, 56%) of the title enol ether (mixture of 2 isomers).

E.
(endo)-(4aα,5α,8α,8aα)-Octahydro-5,8-methanol-1H-benzopyran-3-ol

Under $N_2$, 2.04 g (0.0112 mole) of title D enol ether was stirred 1 hour in 23 ml 20% trifluoroacetic acid. After cooling in an ice bath, ether was added, and the mixture was neutralized by adding solid $NaHCO_3$. The product was extracted with ether. The combined ether extracts were dried over $MgSO_4$, filtered and concentrated to give 1.7 g (0.0101 mol, 90%) of hemi-acetal in the form of a yellow oil.

F.
(endo)-[1α,2α(Z),3α,4α]-7-[(3-Hydroxymethyl)bicyclo[2.2.1]hept-2-yl]-5-heptenoic acid, methyl ester Under $N_2$, 10.6 g of triphenyl carboxybutyl phosphonium bromide was dissolved in 50 ml dimethylsulfoxide (dmso). Potassium t-amylate, 31.8 ml of 1.44M, was added dropwise over 30 minutes, and the mixture stirred 2 hours to give a deep red solution. A solution of 1.7 g (0.0101 mol) title E hemi-acetal in 20 ml THF was added dropwise over 10 minutes. The mixture was stirred overnight.

Acetic acid (1.7 ml, 1.78 g, 0.03 mole) was added to the reaction mixture. Then 30 ml of brine was added and the mixture was acidified to pH 2.5 with concentrated HCl. A white precipitate appeared on stirring at 0°. This was filtered off.

The resulting dmso/brine solution was extracted with 4×50 ml ethyl acetate. Combined ethyl acetate extracts were washed with 4×25 ml $H_2O$, then with 25 ml brine, dried over $MgSO_4$, filtered and concentrated to give a yellow oil. This was dissolved in 125 ml 5% $K_2CO_3$, giving a cloudy solution and precipitate. The solution was filtered, cooled in an ice bath, and acidified to pH 1 with 10% HCl. It was then extracted with 3×50 ml ethyl acetate. The combined ethyl acetate extracts were dried over $MgSO_4$, filtered, and concentrated to give a yellow oil, which was dissolved in ether and reacted with excess $CH_2N_2$ (prepared using 4 g 1-methyl-3-nitro-1-nitrosoguanidine (MNNG), 12 ml 40% KOH and 50 ml $Et_2O$). Acetic acid was added to destroy excess $CH_2N_2$. The ether solution was washed with 5% $NaHCO_3$, dried over $MgSO_4$, filtered and concentrated to give an oil which was purified on a flash column using 20% ethyl acetate in hexane, to give 320 mg title enol ether (1.2 mmol, 12% from title D hydroxymethyl compound).

G.

(endo)-[1α,2α(Z),3α,4α]-7-[(3-Formyl)bicyclo[2.2.1]hept-2-yl]-5-heptenoic acid, methyl ester Under nitrogen, 0.87 g $CrO_3$ (8.7 mmol) was added to a solution of 1.4 ml pyridine in 50 ml $CH_2Cl_2$. The mixture was stirred 30 minutes, giving a brick red solution. Dry celite (2.76 g) was added, followed by dropwise addition of a solution of 460 mg title F enol ether (0.0017 mole) in 10 ml $CH_2Cl_2$. After stirring for 1 hour, the mixture was filtered through celite, and the $CH_2Cl_2$ solution washed with 2×20 ml saturated $NaHCO_3$, 2×20 ml 10% HCl, and 1×saturated $NaHCO_3$. It was then dried over $MgSO_4$, filtered and concentrated to give 360 mg of title aldehyde (0.0014 mole, 78%).

H.

[1α,2α(Z),3β,4α]-7-[(3-Formyl)-bicyclo[2.2.1]hept-2-yl]-5-heptenoic acid, methyl ester In 25 ml methanol, the title G aldehyde (360 mg) was stirred with 30 mg sodium methoxide for 90 minutes. The mixture was poured into 25 ml saturated $NH_4Cl$ and extracted with $CH_2Cl_2$. The $CH_2Cl_2$ extracts were washed with brine, dried over $MgSO_4$, filtered and concentrated to give 310 mg of title aldehyde (86%).

I.

[1α,2α(Z),3β(E),4α]-7-[3-(3-Cyclohexyl-3-oxo-1-propenyl)bicyclo[2.2.1]hept-2-yl]-5-heptenoic acid, methyl ester Under argon, 63 mg of 59.2% NaH in mineral oil was suspended in 10 ml THF. The mixture was cooled in an ice bath and 0.4 g of dimethyl(2-oxo-2-cyclohexyl ethyl)phosphonate was added dropwise in 1 ml THF. The mixture was stirred 15 minutes to give a homogeneous clear solution. The title H aldehyde (410 mg, 1.55 mmol) was added in 2 ml THF. The mixture was stirred 45 minutes, when tlc showed all starting material had disappeared.

The reaction was quenched with 0.2 ml acetic acid, poured into 20 ml water and extracted with ether. The combined ether extracts were washed with water, saturated $NaHCO_3$ and brine. The water layers were both extracted with ether. The combined ether extracts were dried over $MgSO_4$, filtered and concentrated. The resulting oil was purified on a flash column, using 5% ethyl acetate in hexane as eluant to give 170 mg of title I enone (0.46 mmol, 30%).

J.

[1α,2β(Z),3β(1E),4α]-7-[3-(3-Cyclohexyl-3-hydroxy-1-propenyl)bicyclo[2.2.1]hept-2-yl]-5-heptenoic acid, methyl ester The title I enone (170 mg, 0.46 mmol) was dissolved in 4.6 ml methanol and 0.5 ml THF with 0.18 g $CeCl_3.7-H_2O$, under argon, and cooled to −50°. Sodium borohydride (17.8 mg, 0.47 mmol) was added and the reaction stirred 45 minutes at this temperature. The reaction mixture was then poured into 30 ml saturated $NH_4Cl$ and extracted with ethyl acetate. Combined ethyl acetate extracts were dried over $MgSO_4$, filtered and concentrated to give a clear oil. This was purified by flash chromatography, using 5% ethyl acetate in hexane as eluant to give 120 mg (70%) of the title ester-alcohol.

K.

[1α,2α(Z),3β(1E),4α]-7-[3-(3-Cyclohexyl-3-hydroxy-1-propenyl)bicyclo[2.2.1]hept-2-yl]-5-heptenoic acid (fast moving isomer) and

[1α,2α(Z),3β(1E),4α]-7-[3-(3-Cyclohexyl-3-hydroxy-1-propenyl)bicyclo[2.2.1]hept-2-yl]-5-heptenoic acid (slow moving isomer)

The title J ester-alcohol (120 mg) was saponified by stirring with 0.7 ml 1N LiOH, 2 ml THF and 0.5 ml $H_2O$, with methanol added to keep the mixture homogeneous. When tlc showed disappearance of the ester, the mixture was poured into 25 ml saturated NaCl, acidified to pH 2 and extracted with ethyl acetate. The ethyl acetate extracts were dried over $MgSO_4$, filtered and concentrated to give 100 mg clear oil, which was a mixture of diastereomers.

These were separated by repeated chromatography on the analytical hplc using the semi-prep column, packed with 50μ silica gel, eluting with a solvent gradient from 0.25 to 0.5% methanol in methylene chloride, curve 10. This gave 23 mg of the fast-moving isomer (Example 3) and 19.4 mg of the slow-moving isomer (Example 4), 9% yield for title I enone.

EXAMPLE 5

[1α,2β(Z),3β(1E,4S),4α]-7-[3-(3-Hydroxy-3-phenyl-1-propenyl)bicyclo[2.2.1]hept-2-yl]-5-heptenoic acid Following the procedure of Example 1 except substituting benzoic acid for 2-phenylpropionic acid, the title compound is obtained.

EXAMPLE 6

[1α,2β(Z),3β(1E,4S),4α]-7-[3-(3-Hydroxy-4-phenyl-1-butenyl)bicyclo[2.2.1]hept-2-yl]-5-heptenoic acid Following the procedure of Example 1 except substituting phenylacetic acid for 2-phenylpropionic acid, the title compound is obtained.

EXAMPLE 7

[1α,2β(Z),3β(1E,4S),4α]-7-[3-(3-Hydroxy-3-cyclohexyl-1-propenyl)bicyclo[2.2.1]hept-2-yl]-5-heptenoic acid Following the procedure of Example 1 except substituting cyclohexyl carboxylic acid for 2-phenylpropionic acid, the title compound is obtained.

EXAMPLE 8

[1α,2β(Z),3β(1E,4S),4α]-7-[3-(3-Hydroxy-4-cyclopentyl-1-butenyl)bicyclo[2.2.1]hept-2-yl]-5-heptenoic acid Following the procedure of Example 1 except substituting cyclopentylacetic acid for 2-phenylpropionic acid, the title compound is obtained.

EXAMPLE 9

[1α,2β(Z),3β(4S),4α]-7-[3-(3-Hydroxy-4-phenyl-1-pentyl)bicyclo[2.2.1]hept-2-yl]-5-heptenoic acid

A.

[1α,2β(Z),3β(4S),4α]-7-[3-(3-Oxo-4-phenyl-1-pentyl)-bicyclo[2.2.1]hept-2-yl]-5-heptenoic acid, methyl ester To a suspension of 686 mg of purified cuprous bromide (4.8 mmole) in 12 ml of dry THF, cooled at 0°–5° C. was added with stirring 1.35 ml of a 3.5M solution of red-Al (sodium bis(2-methoxyethoxy)aluminumhydride) in toluene dropwise. The solution was stirred at 0°–5° C. for 30 minutes, whereupon it was cooled to −78° C. and 2 ml of n-butanol (18 mmole) was added rapidly, followed by a solution of 476 mg of Example 1 Part I enone (1.2 mmole) in 4 ml of dry THF. After 10 minutes at −78° C., the reaction mixture was warmed to −20° C. and left for an additional one hour. The reaction mixture was quenched by addition of 70 ml of water and then poured into saturated ammonium chloride solution and was extracted with ether (×3). The ether extract was dried over anhydrous magnesium sulfate, filtered and the filtrate was concentrated under reduced pressure. 480 Mg of desired title ketone was obtained (100% yield) as a colorless oil.

B.

[1α,2β(Z),3β(4S),4α]-7-[3-(3-Hydroxy-4-phenyl-1-pentyl)bicyclo[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (∼1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO4 and concentrated under reduced pressure. The crude residue is chromatographed on a silica gel column and eluted with 30–50% ethyl acetate in hexane to obtain the desired title 3R-alcohol.

C.

[1α,2β(Z),3β(4S),4α]-7-[3-(3-Hydroxy-4-phenyl-1-pentyl)bicyclo[2.2.1]hept-2-yl]-5-heptenoic acid Following the procedure of Example 1 except substituting the Part B alcohol for the Example 1 Part A alcohol, the title compound is obtained.

EXAMPLE 10

[1α,2β(Z),3β(4S),4α]-7-[3-(3-Hydroxy-3-phenyl-1-propyl)bicyclo[2.2.1]hept-2-yl]-5-heptenoic acid Following the procedure of Example 9 and Example 1 except substituting benzoic acid for 2-phenylpropionic acid, the title compound is obtained.

EXAMPLE 11

[1α,2β(Z),3β(4S),4α]-7-[3-(3-Hydroxy-4-phenyl-1-butyl)bicyclo[2.2.1]hept-2-yl]-5-heptenoic acid Following the procedure of Example 9 and Example 1 except substituting phenylacetic acid for 2-phenylpropionic acid, the title compound is obtained.

EXAMPLE 12

[1α,2β(Z),3β(4S),4α]-7-[3-(3-Hydroxy-3-cyclohexyl-1-propyl)bicyclo[2.2.1]hept-2-yl]-5-heptenoic acid Following the procedure of Example 9 and Example 1 except substituting cyclohexylcarboxylic acid for 2-phenylpropionic acid, the title compound is obtained.

EXAMPLE 13

[1α,2β(Z),3β(4S),4α]-7-[3-(3-Hydroxy-4-cyclopentyl-1-butyl)bicyclo[2.2.1]hept-2-yl]-5-heptenoic acid Following the procedure of Example 9 and Example 1 except substituting cyclopentylacetic acid for 2-phenylpropionic acid, the title compound is obtained.

EXAMPLE 14

(1α,2β,3β,4α)-7-[3-(3-Hydroxy-4-phenyl-1-pentenyl)-bicyclo[2.2.1]hept-2-yl]heptanoic acid

A.

(1α,2β,3β,4α)-7-[3-(Hydroxymethyl)bicyclo[2.2.1]hept-2-yl]heptanoic acid

To 800 mg (3.0 mmole) of the [1α,2β(Z),3β,4α]-7-[3-(hydroxymethyl)bicyclo[2.2.1]hept-2-yl]-5-heptenoic acid, methyl ester as prepared in Example 1 Part G, dissolved in 120 ml of ethyl acetate and 1 ml of acetic acid is added, under an argon atmosphere, 160 mg of 5% Pd on carbon. The argon atmosphere is exchanged for a slight positive pressure of hydrogen and the reaction is stirred for 8 hours at 25°, filtered through a celite plug and evaporated to provide 730 mg (90%) of the title A compound.

B.

(1α,2β,3β,4α)-7-[3-[3-Hydroxy-4-phenyl-1-pentenyl)-bicyclo[2.2.1]hept-2-yl]heptanoic acid Following the procedure of Example 1 except substituting the Part A alcohol for [1α,2β(Z),3β,4α]-7-[3-(hydroxymethyl)bicyclo[2.2.1]hept-2-yl]-5-heptenoic acid, methyl ester, the title product is obtained.

EXAMPLE 15

(1α,2β,3β,4α)-7-[3-(3-Hydroxy-3-phenyl-1-propenyl)-bicyclo[2.2.1]hept-2-yl]heptanoic acid Following the procedure of Examples 14 and 1 except substituting benzoic acid for 2-phenylpropionic acid, the title compound is obtained.

EXAMPLE 16

(1α,2β,3β,4α)-7-[3-(3-Hydroxy-3-cyclohexyl-1-propenyl)bicyclo[2.2.1]hept-2-yl]heptanoic acid Following the procedure of Examples 14 and 1 except substituting cyclohexylcarboxylic acid for 2-phenylpropionic acid, the title compound is obtained.

EXAMPLE 17

(1α,2β,3β,4α)-7-[3-(3-Hydroxy-3-cycloheptyl-1-propenyl)bicyclo[2.2.1]hept-2-yl]heptanoic acid Following the procedure of Examples 14 and 1 except substituting cycloheptyl carboxylic acid for 2-phenylpropionic acid, the title compound is obtained.

EXAMPLE 18

(1α,2β,3β,4α)-7-[3-(3-Hydroxy-4-cyclopentyl-1-butenyl)bicyclo[2.2.1]hept-2-yl]heptanoic acid Following the procedure of Examples 14 and 1 except substituting cyclopentylacetic acid for 2-phenylpropionic acid, the title compound is obtained.

What is claimed is:

1. A method of inhibiting arachidonic acid-induced platelet aggregation and bronchoconstriction, which comprises administering to the circulatory system of a mammalian host an effective amount of a compound having the structural formula

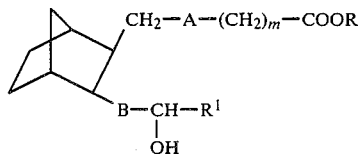

and including all stereoisomers thereof;
wherein A is —$CH_2$—$CH_2$ or —CH=CH—; m is 0 to 5; B is —CH=CH— or $(CH_2)_2$; R is H, lower alkyl, alkali metal or tris(hydroxymethyl)aminomethane; and $R^1$ is aralkyl, cycloalkyl or cycloalkylalkyl or a pharmaceutically acceptable salt thereof.

2. The method as defined in claim 1 wherein said compound is administered in an amount within the range of from about 1 to about 100 mg/kg.

3. The method as defined in claim 1 where in said compound A is CH=CH.

4. The method as defined in claim 1 where in said compound B is CH=CH.

5. The method as defined in claim 1 where in said compound B is —$CH_2CH_2$—.

6. The method as defined in claim 1 where in said compound $R^1$ cycloalkyl.

7. The method as defined in claim 1 where in said compound $R^1$ is aralkyl.

8. The method as defined in claim 1 wherein said compound has the name [1α,2β(Z),3β(1E,4S),4α]-7-[3-(3-hydroxy-4-phenyl-1-pentenyl)bicyclo[2.2.1]hept-2-yl]-5-heptenoic acid or the methyl or ethyl ester thereof, including all stereoisomers thereof.

9. The method as defined in claim 1 wherein said compound has the name [1α,2β(Z),3β(1E),4α]-7-[3-(3-cyclohexyl-3-hydroxy-1-propenyl)bicyclo[2.2.1]hept-2-yl]-5-heptenoic acid including all stereoisomers thereof.

10. A method of inhibiting bronchoconstriction associated with asthma, which comprises administering to a mammalian host an effective amount of a compound having the structural formula

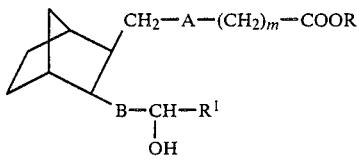

and including all stereoisomers thereof;
wherein A is —$CH_2$—$CH_2$ or —CH=CH—; m is 0 to 5; B is —CH=CH— or $(CH_2)_2$; R is H, lower alkyl, alkali metal or tris(hydroxymethyl)aminomethane; and $R^1$ is aralkyl, cycloalkyl or cycloalkylalkyl or a pharmaceutically acceptable salt thereof.

11. A method for treating peripheral vascular disease, which comprises topically or systemically administering to a mammalian host an effective amount of a compound having the structural formula

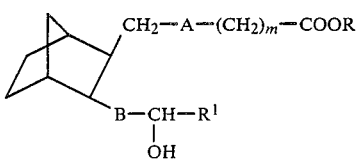

and including all stereoisomers thereof;
wherein A is —$CH_2$—$CH_2$ or —CH=CH—; m is 0 to 5; B is —CH=CH— or $(CH_2)_2$; R is H, lower alkyl, alkali metal or tris(hydroxymethyl)aminomethane; and $R^1$ is aralkyl, cycloalkyl or cycloalkylalkyl or a pharmaceutically acceptable salt thereof.

* * * * *

UNITED STATES PATENT AND TRADEMARK OFFICE
CERTIFICATE OF CORRECTION

PATENT NO. : 4,542,160

DATED : September 17, 1985

INVENTOR(S) : Peter W. Sprague et al.

It is certified that error appears in the above-identified patent and that said Letters Patent is hereby corrected as shown below:

Column 7, line 45, under the structure insert --G--.

Signed and Sealed this

Fourth Day of November, 1986

[SEAL]

*Attest:*

DONALD J. QUIGG

*Attesting Officer*     *Commissioner of Patents and Trademarks*